| United States Patent [19] | [11] Patent Number: 4,659,813 |
| Browning et al. | [45] Date of Patent: Apr. 21, 1987 |

[54] CRYSTALLIZATION PROCESS FOR CEFTAZIDIME DERIVATIVE

[75] Inventors: Ronald C. Browning, Greenwood; Melvin G. Pleiss, Jr., Indianapolis, both of Ind.

[73] Assignee: Eli Lilly and Company, Indianapolis, Ind.

[21] Appl. No.: 801,110

[22] Filed: Nov. 22, 1985

Related U.S. Application Data

[63] Continuation of Ser. No. 669,482, Nov. 8, 1984, abandoned.

[51] Int. Cl.$^4$ .................. C07D 499/44; A61K 31/545
[52] U.S. Cl. .................................................. 540/225
[58] Field of Search .................. 544/25; 514/203, 206; 540/225

[56] References Cited

U.S. PATENT DOCUMENTS 4,258,041  3/1981  O'Callaghan et al. .............. 424/246
4,329,453  5/1982  Brodie et al. .......................... 544/25

Primary Examiner—Nicholas S. Rizzo
Attorney, Agent, or Firm—William B. Scanlon; Leroy Whitaker

[57] ABSTRACT

Ceftazidime pentahydrate is obtained in purified crystalline form in a process comprising acidification of an aqueous solution of ceftazidime to about the optimum pH for nucleation of between about 4.0 and about 4.7 and maintenance at the optimum pH during crystallization. The crystalline product obtained exhibits enhanced stability toward polymer formation when stressed.

8 Claims, No Drawings

CRYSTALLIZATION PROCESS FOR CEFTAZIDIME DERIVATIVE

This application is a continuation of application Ser. No. 669,482 filed Nov. 11, 1984 now abandoned.

BACKGROUND OF THE INVENTION

This invention relates to a process for obtaining in crystalline form the cephalosporin antibiotic known as ceftazidime. In particular, it relates to a crystallization process for the pentahydrate form of ceftazidime.

The semi-synthetic cephalosporin antibiotic ceftazidime, chemically named (6R,7R)-7-[(Z)-2-(2-aminothiazol-4-yl)-2-(2-carboxyprop-2-oxyimino)acetamido]-3- C(1-pyridiniummethyl)-ceph-3described by U.S. Pat. No. 4,258,041. The pentahydrate form of ceftazidime is a useful pharmaceutical form of the antibiotic and is described by U.S. Pat. No. 4,329,453.

SUMMARY OF THE INVENTION

This invention provides a process for the preparation of high quality crystalline ceftazidime pentahydrate having increased bulk powder density and enhanced stability. The process comprises preparing an aqueous solution of ceftazidime at a temperature between about 5° C. and about 15° C. by adjusting the pH of a cold solution of a salt of ceftazidime or of a suspension of ceftazidime pentahydrate to a pH of about 5.5 to about 6.5. The cold aqueous solution is acidified to a pH of optimum nucleation of about 4.0 to about 4.7, and thereafter the pH is maintained during crystallization at the optimum nucleation pH.

The process provides ceftazidime pentahydrate of high purity, enhanced stability, and of high bulk powder density. Ceftazidime in the free base form or its dihydrochloride or dihydrobromide salts, can be employed in the process to obtain the purified pentahydrate form.

DETAILED DESCRIPTION

Ceftazidime, in the form of its crystalline pentahydrate, is a preferred pharmaceutical form of the antibiotic. However, crystalline pentahydrate is difficult to prepare in highly pure form. Formulations of impure ceftazidime pentahydrate have been found to be unstable. For example, it has been found that when impure ceftazidime pentahydrate or amorphous ceftazidime is subjected to elevated temperatures (60° C. for three days), the antibiotic decomposes with the formation of high molecular weight (>10,000) polymeric substances. Such polymerization also may occur during prolonged storage of impure or amorphous ceftazidime. These polymers decrease the pharmaceutical elegance of the product. Because of the instability of impure ceftazidime pentahydrate, there is a need for a method to obtain substantially pure ceftazidime pentahydrate for pharmaceutical use.

During the study of the crystallization of ceftazidime pentahydrate, it was found that the purity of the crystalline pentahydrate increases when the crystallization is carried out at a pH greater than 4.0. It has also been found that ceftazidime pentahydrate will crystallize from aqueous solutions at a pH of about 3.5 to 4.0 and that as crystallization occurs, the pH of the ceftazidime solution increases and, if uncontrolled, may rise to a pH of about 5 or greater. In carrying out the process of the present invention, it has been found that the rate of nucleation and crystallization of the pentahydrate can be controlled at an optimum pH of about 4.0 to about 4.7, preferably at about pH 4.4 to 4.6, to provide substantially pure crystalline ceftazidime pentahydrate.

According to the process of this invention, ceftazidime is obtained as the crystalline pentahydrate in highly pure form with enhanced stability toward decomposition to high molecular weight polymeric substances. The crystalline pentahydrate obtained has a higher bulk powder density than previously obtainable ceftazidime pentahydrate. The process of this invention comprises a controlled crystallization of the pentahydrate from a cold aqueous solution at the acidic pH at which the optimum rate of nucleation of the pentahydrate crystals occurs. In carrying out the process, an aqueous solution of ceftazidime is prepared by adjusting the pH of a cold aqueous suspension or solution to about 5.5 to about 6.5. The solution is maintained at a temperature between about 5° C. and about 15° C. and acidified to a pH above 4.0. At this pH range, the ceftazidime crystallization initiates and the pH rises during crystallization. Careful maintenance of the acidity of the cold aqueous solution at the optimum nucleation pH of about 4.0 to about 4.7 is achieved by the monitored addition of acid. The pH is maintained at this optimum level until crystallization is complete.

The concentration of ceftazidime in the aqueous solution is generally between about 100 mg per ml to about 200 mg per ml, and preferably at about 150 mg per ml. Following the acidification of the cold aqueous ceftazidime solution, the solution may be seeded with crystalline ceftazidime pentahydrate to initiate the crystallization. Once crystallization commences at the lower pH, the pH rises slowly and will continue to rise unless controlled with additional acid.

The acidification of the cold ceftazidime solution to the desired pH and the maintenance of the optimum nucleation pH are achieved by the addition of a suitable acid. In general, any inorganic or organic acid that will be soluble in the cold solution and produce the desired acidity can be used. Mineral acids such as hydrochloric acid, hydrobromic acid, sulfuric acid, and phosphoric acid can be used. Organic acids such as the alkyl carboxylic acids, e.g. formic acid, acetic acid, propionic acid, and the like; halogenated acids such as trichloroacetic acid; sulfonic acids such as the alkyl sulfonic acids, e.g. methanesulfonic acid and ethanesulfonic acid; the arylsulfonic acids, e.g. toluenesulfonic acid and benzenesulfonic acid are suitable for use in the process. Mineral acids are preferred acids for use in the process. Phosphoric acid is a preferred acid. Hydrochloric acid is also a preferred acid for use in the process.

The concentration of the acid used is not critical and the acid may be concentrated or diluted. However, highly diluted acid may result in overly-dilute crystallization solution, thus lowering the yield of crystals obtained.

The optimum nucleation pH is readily maintained with an automatic titration apparatus. The initial pH adjustment to form the aqueous solution of ceftazidime can be achieved with a suitable base such as sodium hydroxide.

Ceftazidime in the form of one of its salts, e.g. its dihydrochloride or dihydrobromide salt or in the form of an impure pentahydrate or amorphous material may be used in the process to obtain the purified crystalline pentahydrate. Accordingly, the process of this invention may be employed to recrystallize impure ceftazidime pentahydrate or it may be used to obtain substantially pure crystalline pentahydrate from the dihydrochloride or dihydrobromide salt form.

Following the completion of the crystallization at the optimum nucleation pH, additional, less pure ceftazidime pentahydrate may be obtained from the mother liquor by lowering the pH to between about 3.5 and about 4.0. However, this increase in yield is offset by a lowering in the quality of the isolated ceftazidime pentahydrate. The purity of the ceftazidime pentahydrate crystals obtained by the crystallization at the controlled nucleation pH is superior to that obtained at the lower pH.

Following the crystallization at the controlled pH, the crystallization mixture is desirably stored for between about 2 and about 12 hours at a temperature of about 5° C. to ensure that crystallization is complete.

The crystalline pentahydrate is then harvested in a conventional manner, e.g. by filtration or centrifugation and is then dried.

The ceftazidime pentahydrate obtained by the process of this invention exhibits a greater degree of stability especially with respect to formation of polymeric substances having a molecular weight of 10,000 or above than does crystalline material precipitated at a lower pH of about 3 to 4. The pentahydrate produced by the process of this invention, when heated in a closed vial at 60° C. for three days, exhibits less tendency to form additional high molecular weight polymer. The percentage by weight of such high molecular weight polymers present in ceftazidime pentahydrate prepared according to the process of the invention is generally on the order of less than 0.1%. When stressed under the aforementioned conditions, these materials generally contain less than 0.5% polymer.

As was mentioned hereinabove, the product produced by the process of this invention has a higher bulk powder density than material obtained by precipitation at uncontrolled pH. For example, in an uncontrolled precipitation of ceftazidime pentahydrate at an initial pH of 3.60, ceftazidime pentahydrate having a bulk density of 0.12 g/ml was obtained, whereas the crystalline ceftazidime pentahydrate obtained by precipitation at controlled pH about 4.4 to about 4.7 generally has a bulk density of about 0.23 g/ml. The higher bulk density renders the ceftazidime pentahydrate more suitable for dry powder filling operations.

The crystalline ceftazidime pentahydrate obtained by the process of this invention is formulated into suitable pharmaceutical formulations for parenteral administration. It can be formulated into suitable unit dosage forms comprising a physiologically acceptable base such as an alkali metal carbonate, especially sodium carbonate in dry powder form, and filled into vials.

The following examples further illustrate the manner in which the process of this invention is carried out.

As used in the Examples, the term "ceftazidime activity" refers to the amount of free ceftazidime, i.e. calculated from the weight of ceftazidime pentahydrate or a salt of ceftazidime. High performance liquid chromatography is abbreviated HPLC.

The HPLC system used to determine the percentage of high molecular weight polymer in ceftazidime pentahydrate employs a gel having an exclusion limit of about 10,000 MW. A suitable gel is Fractogel ® TSK HW-40 (Merck). The assay is carried out in a glass HPLC column measuring 50 cm in length by 0.9 cm i.d. packed with the gel in potassium phosphate solution. A 10 mg sample of the ceftazidime pentahydrate is dissolved in 5 ml of pH 7 phosphate buffer. A 100 microliter portion of the solution is injected and the column is run at room temperature at a flow rate of 1 ml/min. A photometric detector suitable for use in HPLC is run at 0.1 AUFS at 210 nm. The limit of reliable detection in the assay is about 0.06% polymer.

Ceftazidime pentahydrate samples were stressed at a temperature of 60° C. for 3 days in sealed vials (1.2 g; nominally 10 ml capacity).

EXAMPLE 1

Controlled Crystallization of Ceftazidime Pentahydrate

A suspension of 24 g of ceftazidime pentahydrate in 61 ml of water was cooled to about 5° C. and treated with 30.2 ml of 1.28M sodium hydroxide to form a solution (pH 5.9). The solution was filtered and diluted with water to a concentration of 150 mg/ml of ceftazidime activity. A 131 ml aliquot of the above solution (19.6 g of ceftazidime activity, 36.0 mmole) was cooled to and maintained at about 5° C. while the pH was adjusted and maintained at 4.4 over 150 minutes by the controlled addition of 15.5 ml of 2.12M phosphoric acid. The pH of the crystal slurry was adjusted to and maintained at pH 4.2 for an additional 75 minutes by the controlled addition of 1.12 ml of 2.12M phosphoric acid. The crystal slurry was stirred overnight at a temperature of 5° C. and the crystals of ceftazidime pentahydrate harvested by filtration. The harvest pH was 4.3. The crystals were washed with 150 ml of water and with 100 ml of acetone-water (99/1, v/v) and air dried. There were obtained 20.0 g having a potency of 84.2% via HPLC assay. A sample of the crystalline pentahydrate when stressed at 60° C. for three days gave no detectable high molecular weight polymer.

EXAMPLE 2

Controlled Crystallization of Ceftazidime Pentahydrate

A suspension of 47.9 g of ceftazidime pentahydrate in 120 ml of water was treated at about 5° C. with 60 ml of 1.28M sodium hydroxide to form a solution (pH 5.9). The solution was filtered and diluted with water to concentration of 150 mg per ml of ceftazidime activity. A 131 ml aliquot (19.6 g ceftazidime activity; 36 mmole) of the solution was cooled to 5° C. and acidified to pH 4.6 with 2.12M phosphoric acid. The pH was maintained at 4.6 by the controlled addition of 13.6 ml of 2.12M phosphoric acid while the temperature of the solution was maintained at about 5° C. The crystal slurry was allowed to stir overnight at 5° C. and harvested by filtration. The pH of the slurry at harvest was 4.85. The crystals were washed with 600 ml of water followed by 400 ml of acetone-water (99/1, v/v) and air dried. There were obtained 15.1 g of crystalline ceftazidime pentahydrate assaying 85.0% for ceftazidime via HPLC assay. A sample on the product when stressed at 60° C. for three days gave no detectable high molecular weight polymer content.

EXAMPLE 3

Uncontrolled Crystallization of Ceftazidime Pentahydrate

A suspension of 75 g of ceftazidime pentahydrate in 180 ml of water was treated at about 5° C. to 10° C. with 93 ml of 1.28M sodium hydroxide to form a solution (pH 5.9). The solution was filtered and diluted with water to a concentration of 150 mg/ml of ceftazidime activity. A 132 ml aliquot of the solution was cooled to and maintained at 5° C. while the pH was adjusted to 3.35 with 17.1 ml of 2.12M phosphoric acid. The acidified solution was seeded and allowed to crystallize overnight at a temperature of about 5° C. The crystals were harvested by filtration. The pH of the slurry at harvest was 3.65. The crystals were washed with 150 ml of water and with 100 ml of acetone-water (99/1, v/v) and air dried. There were obtained 20 g of crystalline ceftazidime pentahydrate assaying for 81.3% ceftazidime activity (HPLC). A sample of the product when stressed at 60° C. for three days underwent extensive decomposition. The product contained 0.15% high molecular weight polymer content. When the product was stressed at 60° C. for three days, extensive decomposition occurred.

Controlled Crystallization

Another 132 ml aliquot of the ceftazidime solution prepared as described above was acidified at a controlled pH of 4.7 to provide ceftazidime pentahydrate containing no detectable high molecular weight polymer. When stressed at 60° C. for three days, the product showed 0.54% of high molecular weight polymer.

EXAMPLE 4

Controlled Crystallization With Formic Acid

A suspension of 48 g of ceftazidime pentahydrate in 120 ml of water was treated with 60 ml of 1.26M sodium hydroxide at 5° C. to 10° C. to form a solution. The solution was filtered and diluted with water to a concentration of 150 mg of ceftazidime activity per milliliter. A 128 ml aliquot of the solution (19.2 g activity, 35.2 mmole) was cooled to and maintained at a temperature of 5° C. while the pH was adjusted to and controlled at 4.5 over four hours by the addition of 5.9M formic acid (6.67 ml were required). Ceftazidime pentahydrate seed crystals were added to the stirred solution after the initial pH adjustment to 4.5 and crystallization commenced. After the four hours at controlled pH the crystals were harvested by filtration, washed with 150 ml of chilled water and with 120 ml of chilled acetone and air dried to provide 18.0 g of ceftazidime pentahydrate. The material assayed as follows: HPLC potency 83.7% ; polymer (stressed) 0.12%; related substances 0.70% ; Karl Fischer 13.9%.

Uncontrolled Crystallization With Formic Acid

A second 128 ml aliquot of the ceftazidime solution prepared as described above was cooled and maintained at 5° C., while the pH was adjusted from 5.8 to 3.6 with 10.5 ml of 5.9M formic acid. The stirred solution was seeded with ceftazidime pentahydrate crystals and crystallization commenced. After 5 hours the crystals were harvested by filtration, washed with 150 ml of chilled water and 100 ml of chilled acetone and air dried to give 20.8 g of ceftazidime pentahydrate. The material assayed as follows: HPLC potency 84.4% (as is); polymer (stressed material) 0.66%; related substances, 1.07%; Karl Fischer 14.1%.

EXAMPLE 5

Controlled Crystallization

A suspension of 48 g of impure ceftazidime pentahydrate in 120 ml of water was colled to a temperature of between 5° C. to 10° C. and treated with 59 ml of 1.26M sodium hydroxide. The solution was filtered and diluted with water to a concentration of 150 mg of ceftazidime activity per milliliter. A 131 ml aliquot of the solution (containing 36.0 mmole) was cooled and maintained at about 5° C. while the pH was adjusted to and controlled at 4.5 over 4.5 hours. The initial acidification and maintenance of pH 4.5 required a total of 13.3 ml of 1.83M hydrochloric acid. Ceftazidime pentahydrate seed crystals were added to the solution after the initial pH adjustement and crystallization commenced.

The crystal slurry was stirred overnight in the cold after which the pH was 4.65. The crystals were harvested by filtration, washed with 150 ml of chilled water and with 100 ml of chilled acetone, and air dried to yield 15.4 g of ceftazidime pentahydrate as large, well-shaped, rectangular platelets. Assays: HPLC potency, 83.5%; polymer (stressed), none detected; related substances, 0.7%; Karl Fischer, 13.8%.

Uncontrolled Crystallization

Another 131 ml aliquot of the ceftazidime solution prepared as described above was adjusted to and maintained at 5° C. and the pH adjusted to 3.5 with 15.2 ml of 1.83M hydrochloric acid. The stirred solution was seeded with ceftazidime pentahydrate crystals and crystallization began. After one hour, the pH of the crystal slurry was readjusted from 4.55 to 3.50 with an additional 2.90 ml of 1.83M hydrochloric acid. The slurry was stirred for three more hours and then filtered. The crystals were washed with 150 ml of chilled water and 100 ml of chilled acetone and air dried. There were obtained 19.3 g of ceftazidime pentahydrate which assayed as follows: HPLC potency, 83.2% (as is); polymer (stressed), 0.82%; related substances, 1.04%; Karl Fischer, 13.9%.

We claim:

1. A process for preparing ceftazidime pentahydrate in crystalline form which comprises acidifying an aqueous solution of ceftazidime having a pH between about 5.5 and about 6.5 to a pH of between about 4.0 and about 4.7 at a temperature between about 5° C. and about 15° C., and maintaining during crystallization the acidity of said solution by controlled acidification at a pH between about 4.0 and about 4.7.

2. The process of claim 1 wherein the pH is maintained at between about 4.4 and about 4.6.

3. The process of claim 1 wherein a mineral acid is used for controlled acidification.

4. The process of claim 3 wherein the acid is phosphoric acid.

5. The process of claim 3 wherein the acid is hydrochloric acid.

6. The process of claim 1 wherein the concentration of the solution of ceftazidime is between about 100 mg/ml and about 200 mg/ml.

7. The process of claim 6 wherein the concentration is 150 mg/ml.

8. The process of claim 1 wherein formic acid is used.

* * * * *